United States Patent
Carminati

(10) Patent No.: US 6,441,039 B1
(45) Date of Patent: *Aug. 27, 2002

(54) GASTRO-INTESTINAL ADVERSE EFFECT-FREE COMPOSITION COMPRISING AN L-CARNITINE REPLACEMENT

(75) Inventor: Paolo Carminati, Milan (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

This patent is subject to a terminal disclaimer.

(21) Appl. No.: 09/740,787

(22) Filed: Dec. 21, 2000

Related U.S. Application Data

(63) Continuation of application No. PCT/EP99/04380, filed on Jun. 24, 1999.

(30) Foreign Application Priority Data

Jun. 25, 1998 (EP) ............................................ 98830383

(51) Int. Cl.⁷ .................... A61K 31/195; A61K 31/225; A61K 31/205
(52) U.S. Cl. ........................ 514/561; 514/547; 514/556; 514/922
(58) Field of Search ................................. 514/547, 561, 514/556, 922

(56) References Cited

U.S. PATENT DOCUMENTS 4,602,039 A   7/1986   Cavazza
6,013,670 A * 1/2000   Cavazza ..................... 514/547

FOREIGN PATENT DOCUMENTS

EP   0 637 449 A   2/1995
FR   2 529 545 A   1/1984

* cited by examiner

*Primary Examiner*—Raymond Henley, III
*Assistant Examiner*—Donna Jagoe
(74) *Attorney, Agent, or Firm*—Nixon & Vanderhye P.C.

(57) ABSTRACT

Exogenous L-carnitine in the form of an equimolar amount of L-carnitine acid fumarate is administered to reduce increased volume and fluidity of stools and frequency of bowel movements relative to their usual pattern brought about by the administration of exogenous L-carnitine. Preferably nutritionally dietetically or therapeutically effective amount of L-carnitine acid fumarate is administered orally in the form of a tablet pill, capsule or powder.

4 Claims, No Drawings

GASTRO-INTESTINAL ADVERSE EFFECT-FREE COMPOSITION COMPRISING AN L-CARNITINE REPLACEMENT

This is a Continuation of PCT/EP99/04380, filed Jun. 24, 1999.

The present invention relates to a method for reducing and counteracting gastrointestinal disorders brought about by the intake of L-carnitine in an individual in need thereof. More specifically, the present invention relates to a method for reducing and counteracting increased volume and fluidity of stools and frequency of bowel movements relative to the individual's usual pattern following intake of exogenous L-carnitine for therapeutic, nutritional or dietetic purposes.

As is well known, therapeutical uses of L-carnitine inner salt (hereinbelow, simply "L-carnitine") have long since been known. For instance, L-carnitine has been used in the cardiovascular field for the treatment of acute and chronic myocardial ischaemia, angina pectoris, heart failure and cardiac arrhythmias.

In the nephrological field, L-carnitine has been administered to chronic uraemic patients undergoing regular haemodialytic treatment to combat myasthenia and the onset of muscular cramps.

Other therapeutic uses relate to the normalisation of the HDL:(LDL+VLDL) ratio and total parenteral nutrition.

Besides the aforesaid uses in the therapeutical field, L-carnitine has increasingly established itself on the so-called health food, medical food or nutraceutical market. These terms, which have yet to be rigorously defined from the regulatory point of view, denote foods or food components such as food supplements, dietetic products, energy foods, and the like, i. e. formulations which are not addressed to mainly or exclusively therapeutic purposes but which are aimed rather at enhancing well-being and at producing a general improvement in fitness and performance on the part of the consumer or at preventing metabolic disorders caused by dietary deficiencies or by the inadequate biosynthesis of essential endogenous substances as a result of advancing age.

The growing interest in L-carnitine in this field, too, stems from the increasingly widespread recognition, coroborated by scientific evidence, that L-carnitine, in addition to its well-known therapeutic value in the treatment of various diseases, makes a marked contribution towards supplying energy to the skeletal musculature and increasing resistance to prolonged, intense stress in professional athletes or in any subject practising sport also at amateur level, enhancing the performance capability of such subjects.

In addition, L-carnitine constitutes an indispensable nutritional supplement for vegetarians, whose diets have a low carnitine content as well as a low content of the two amino acids, lysine and methionine, which are the precursors of the biosynthesis of L-carnitine in the kidneys and liver.

The same considerations apply not only to those subjects who have feel debilitated, experiencing a particular state of stress or physical and/or mental fatigue.

Particularly but not exclusively for the aforesaid applications in the nutritional/dietetic field, solid, orally administrable L-carnitine-containing compositions are the preferred presentation form, inasmuch as they make it particularly easy for the users to take the active ingredient and comply with optimal dosage regimens. Since L-carnitine is a highly hygroscopic compound, the preparation of solid compositions entails complex problems of processing, stability and storage both of the raw material and of the finished products.

For instance, L-carnitine tablets have to be packaged in blisters to keep them out of contact with the air, since, otherwise, even in the presence of normal humidity conditions, they would undergo alterations, swelling up and becoming pasty and sticky.

L-carnitine hygroscopicity has prompted considerable efforts in synthesising non-hygroscopic salts which are solid and stable, particularly even in conditions of prolonged storage, which can therefore be easily processed and formulated with the usual excipients, using blending, tablettting devices, etc., of a traditional type, and which, in addition, pose no packaging problems when converted into finished products.

To date, two L-carnitine salts have been developed and marketed which overcome the hygroscopicity drawback entailed by L-carnitine: L-carnitine L-tartrate and L-carnitine acid fumarate.

Apart, however, from the hygroscopicity problem, L-carnitine presents a further bothersome drawback to L-carnitine users: episodes of diarrhoea have been frequently reported (see e.g. Martindale, The Extra Pharmacopoeia, $31^{st}$ Edition, 1996, page 356, and Drug Information for the Health Care Professional, $18^{th}$ Edition, 1998, page 1856) whose number is bound to increase having regard to the steadily growing population of L-carnitine users.

This adverse effect is dose-related and may only be reduced by decreasing (e.g. by halving) the dose of L-carnitine. This drastic reduction is, however, in disagreement with recent recommendations having regard to the role of L-carnitine as a energizing nutrient which provide for a daily intake of up to 4 grams for L-carnitine to be effective (Crayhon R., The carnitine miracle, M. Evans and Company, Inc., New York, 1998, page 61).

Replacement of L-carnitine with L-carnitine L-tartrate may even worsen the aforesaid adverse effect. This is far from being surprising since:

"Tartaric acid is used . . . as a saline purgative. Strong solutions of tartaric acid are mildly irritant and if ingested undiluted may cause violent vomiting, diarrhoea and abdominal pain".

(Martindale, loc. cit., page 1757)

Apart from the aforesaid gastrointestinal adverse effect, large doses of tartaric acid should be avoided also because they may cause renal damage (Goodman, L. & Gilman, A.: The pharmacological basis of therapeutics. MacMillan, New York, 1965, $3^{rd}$ ed., p. 818; The Merck Index, New Jersey, 1960, $7^{th}$ ed., p. 1012; Sollman, T.: A manual of pharmacology, Saunders, 1957, $8^{th}$ ed., p. 1055).

Also a fatal case of human tartrate nephropathy was reported (Robertson B. et al., Acta Path. Microbiol. Scandinav. 74, 305–310, 1968).

The intake of large doses of L-carnitine (up to 4 grams/day) in the form of L-carnitine L-tartrate would, therefore, seem unsafe having regard to the remarkable amount of tartaric acid which should be ingested, too.

There is, therefore, the need of providing an L-carnitine replacement, i.e. an L-carnitine derivative, which, while on one hand maintaining the useful and beneficial therapeutical, nutritional and dietary properties of L-carnitine, is free of the aforesaid troublesome adverse effect shown by both L-carnitine and L-carnitine-L-tartrate.

The object of the present invention is to provide such L-carnitine replacement.

It has now been found that L-carnitine acid fumarate is such adverse effect-free L-carnitine replacement.

Accordingly, the present invention relates to the use of L-carnitine acid fumarate for preparing an orally administrable composition for supplying exogenous L-carnitine to individuals in need thereof who, following L-carnitine intake, would experience an increased volume and fluidity of stools and frequency of bowel movements relative to their usual pattern.

It is apparent that the aforesaid orally administrable composition may be used as a dietary supplement, a nutraceutical or a pharmaceutical specialty.

According to a further aspect of the present invention, a method is provided for reducing an increased volume and fluidity of stools and frequency of bowel movements relative to an individual's usual pattern which would be brought about by the administration of exogenous L-carnitine to the individual in need thereof, which comprises administering to said individual the required amount of exogenous L-carnitine in the form of an equimolar amount of L-carnitine acid fumarate.

L-carnitine acid fumarate is a highly stable and non-hygroscopic L-carnitine salt whose preparation and physico-chemical properties are disclosed in U.S. Pat. No. 4,602,039 (to Cavazza) which is incorporated herein by reference.

On the grounds of these properties, L-carnitine acid fumarate lends itself to the preparation of dietetic, nutritional or pharmaceutical compositions, in particular solid compositions, which, differently from L-carnitine- or L-carnitine L-tartrate containing compositions, are totally free of gastrointestinal adverse effects.

A study on the effect on intestinal motility of L-carnitine acid fumarate vs. L-carnitine L-tartrate administered by the oral route to the rat at a single dose, using the charcoal propulsion test, is hereinbelow reported.

35-day old, Hsd Sprague Dawley (SD) male rats (Harlan), weighing 125–150 g were used in the study. The rats were supplied by Harlan Nossan S.r.l., 8, Via E. Fermi, 20050 Correzzana (MI)—Italy.

Eight male rats/group were treated orally with L-Carnitine acid Fumarate, at the doses of 430–855 and 1710 mg/10 ml/kg, and with L-Carnitine L-Tartrate at the doses of 365–730 and 1455 mg/10 ml/kg.

The doses of the two compounds were chosen as equimolar to 250–500 and 1000 mg/kg of L-Carnitine Inner Salt.

Two additional groups, each consisting of eight males, were set up and orally treated respectively with the vehicle (Control group—0.5% Carboxymethylcellulose (MC) in deionized water: 10 ml/kg) or with Atropine (30 mg/10 ml/kg) as reference standard.

The animals were subdivided at random (in number of 4/cage) into the different dosage groups according to the following scheme:

| GROUP | ORAL TREATMENT | DOSE |
|---|---|---|
| 1 | Vehicle (0.5% CMC) | — |
| 2 | L-Carnitine Fumarate | 430 |
| 3 | L-Carnitine Fumarate | 855 |
| 4 | L-Carnitine Fumarate | 1710 |
| 5 | L-Carnitine Tartrate | 365 |
| 6 | L-Carnitine Tartrate | 730 |
| 7 | L-Carnitine Tartrate | 1455 |
| 8 | Atropine Sulphate Salt | 30 |

Forty-five minutes after the administration of all the above reported substances, each rat received orally 1.5 ml of a 10% charcoal suspension.

Exactly twenty minutes after dosing with charcoal suspension the rats were sacrificed; then the distance the charcoal meal had travelled throughout the intestine (from the pyloric sphincter towards the caecum) was measured and expressed as a percentage of the total gut length.

Results (see Table 1 and Appendixes 1a through 1d)

L-Carnitine acid Fumarate

No statistically significant differences were seen between the treated groups and the one receiving the vehicle for the distance travelled by charcoal, as % of total intestine length. No particular trend was seen for the different doses administered.

L-Carnitine L-Tartrate

As for the L-carnitine L-tartrate, a statistically significant ($p<0.05$) increase of gastrointestinal motility was seen in the middle and high dosage groups (730 and 1455 mg/kg, respectively) when compared with control group; an evident relationship between the administered dose and the distance the charcoal had travelled throughout the intestine was present.

Atropine

The group treated with Atropine (30 mg/kg) showed a statistically highly significant ($p<0.001$) decrease in gastrointestinal motility, as expected.

CONCLUSIONS

In conclusion, under the adopted experimental conditions the test article L-carnitine acid fumarate administered orally in single dose to the rat did not cause a change in gastrointestinal motility at any tested dose.

As for the L-carnitine L-tartrate a statistically significant increase in gastrointestinal motility was detected in the middle and high dosage groups, when compared with controls, with an evidence of dose-relationship.

TABLE 1

Effect of oral administration of test articles L-Carnitine Fumarate and L-Carnitine Tartrate on gastrointestinal motility in the Sprague Dawley rat

| Group no. | | Bodyweight (g) | Distance travelled as % of total intestine length | % change from vehicle |
|---|---|---|---|---|
| 1 | | | | |
| Vehicle: 0.5% CMC in deionized water | Mean | 213.50 | 62.41 | — |
| | ±S.E. | 256 | 1.64 | |
| | n | 8 | 8 | |

TABLE 1-continued

Effect of oral administration of test articles L-Carnitine Fumarate and L-Carnitine Tartrate on gastrointestinal motility in the Sprague Dawley rat

| Group no. | | Bodyweight (g) | Distance travelled as % of total intestine length | % change from vehicle |
|---|---|---|---|---|
| 2 | | | | |
| L-Carnitine acid Fumarate: 430 mg/10 ml/kg | Mean | 207.75 | 65.76 | +5.37 |
| | ±S.E. | 2.51 | 3.94 | |
| | n | 8 | 8 | |
| 3 | | | | |
| L-Carnitine acid Fumarate: 855 mg/10 ml/kg | Mean | 207.63 | 58.66 | −6.01 |
| | ±S.E. | 6.50 | 2.63 | |
| | n | 8 | 8 | |
| 4 | | | | |
| L-Carnitine acid Fumarate: 1710 mg/10 ml/kg | Mean | 211.25 | 64.57 | +3.47 |
| | ±S.E. | 3.86 | 3.68 | |
| | n | 8 | 8 | |
| 5 | | | | |
| L-Carnitine L-Tartrate: 365 mg/10 ml/kg | Mean | 212.38 | 62.72 | +0.49 |
| | ±S.E. | 3.85 | 2.06 | |
| | n | 8 | 8 | |
| 6 | | | | |
| L-Carnitine L-Tartrate: 730 mg/10 ml/kg | Mean | 209.38 | 70.86■ | +13.53 |
| | ±S.E. | 3.23 | 2.89 | |
| | n | 8 | 8 | |
| 7 | | | | |
| L-Carnitine L-Tartrate: 1455 mg/10 ml/kg | Mean | 212.13 | 75.34■ | +20.72 |
| | ±S.E. | 3.77 | 4.94 | |
| | n | 8 | 8 | |
| 8 | | | | |
| Reference article: Atropine 30 mg/10 ml/kg | Mean | 209.88 | 43.15▲ | −30.87 |
| | ±S.E. | 1.90 | 1.30 | |
| | n | 8 | 8 | | n = number of animals
Student's "t" test vs control group: ■ and ▲ indicate $p < 0.05$ and $p < 0.001$, respectively

| Rat no. | Body-weight (g) | Length of intestine (cm) | Distance travelled by charcoal (cm) | Distance travelled as % of total intestine length |
|---|---|---|---|---|
| Appendix 1a | | | | |
| Effect of oral administration of test articles L-Carnitine acid Fumarate and L-Carnitine L-Tartrate on gastrointestinal motility in the Sprague Dawley rat | | | | |
| Group no. 1: 0.5% CMC in deionized water | | | | |
| 1 | 209 | 108 | 62 | 57.41 |
| 2 | 201 | 109 | 62 | 56.88 |
| 3 | 216 | 108 | 64 | 59.26 |
| 4 | 203 | 120 | 84 | 70.00 |
| 5 | 222 | 123 | 83 | 67.48 |
| 6 | 216 | 115 | 72 | 62.61 |
| 7 | 218 | 119 | 76 | 63.87 |
| 8 | 220 | 123 | 76 | 61.79 |
| Group no. 2: L-Carnitine acid Fumarate: 430 mg/10 ml/kg | | | | |
| 9 | 196 | 124 | 78 | 62.90 |
| 10 | 202 | 123 | 79 | 64.23 |
| 11 | 216 | 121 | 72 | 59.50 |
| 12 | 203 | 119 | 92 | 77.31 |
| 13 | 215 | 121 | 91 | 75.21 |
| 14 | 208 | 126 | 92 | 73.02 |
| 15 | 208 | 117 | 83 | 70.94 |
| 16 | 214 | 114 | 49 | 42.98 |
| Appendix 1b | | | | |
| Effect of oral administration of test articles L-Carnitine acid Fumarate and L-Carnitine L-Tartrate on gastrointestinal motility in the Sprague Dawley rat | | | | |
| Group no. 3: L-Carnitine acid Fumarate: 855 mg/10 ml/kg | | | | |
| 17 | 217 | 125 | 75 | 60.00 |
| 18 | 165 | 115 | 61 | 53.04 |
| 19 | 217 | 122 | 79 | 64.75 |
| 20 | 199 | 104 | 52 | 50.00 |
| 21 | 215 | 130 | 64 | 49.23 |
| 22 | 212 | 116 | 77 | 66.38 |
| 23 | 216 | 126 | 86 | 68.25 |
| 24 | 220 | 125 | 72 | 57.60 |
| Group no. 4: L-Carnitine acid Fumarate: 1710 mg/10 ml/kg | | | | |
| 25 | 222 | 130 | 84 | 64.62 |
| 26 | 204 | 115 | 80 | 69.57 |
| 27 | 220 | 117 | 70 | 59.83 |
| 28 | 212 | 122 | 82 | 67.21 |
| 29 | 226 | 124 | 95 | 76.61 |
| 30 | 203 | 117 | 84 | 71.79 |
| 31 | 209 | 114 | 74 | 61.91 |

-continued

| 32 | 194 | 126 | 53 | 42.06 |

Appendix 1c
Effect of oral administration of test articles L-Carnitine acid Fumarate and L-Carnitine L-Tartrate on gastrointestinal motility in the Sprague Dawley rat Group no. 5: L-Carnitine L-Tartrate: 365 mg/10 ml/kg

| 33 | 208 | 104 | 62 | 59.62 |
| 34 | 213 | 114 | 71 | 62.28 |
| 35 | 217 | 119 | 81 | 68.07 |
| 36 | 193 | 121 | 76 | 62.81 |
| 37 | 204 | 118 | 75 | 63.56 |
| 38 | 225 | 123 | 65 | 52.85 |
| 39 | 213 | 123 | 74 | 60.16 |
| 40 | 226 | 116 | 84 | 72.41 |

Group no. 6: L-Carnitine L-Tartrate: 730 mg/10 ml/kg

| 41 | 191 | 123 | 89 | 72.36 |
| 42 | 215 | 128 | 92 | 71.88 |
| 43 | 207 | 123 | 101 | 82.11 |
| 44 | 212 | 126 | 100 | 79.37 |
| 45 | 203 | 127 | 71 | 55.91 |
| 46 | 213 | 121 | 78 | 64.46 |
| 47 | 221 | 133 | 94 | 70.68 |
| 48 | 213 | 117 | 82 | 70.09 |

Appendix 1d
Effect of oral administration of test articles L-Carnitine acid Fumarate and L-Carnitine L-Tartrate on gastrointestinal motility in the Sprague Dawley rat Group no. 7: L-Carnitine L-Tartrate: 1455 mg/10 ml/kg

| 49 | 228 | 130 | 104 | 80.00 |
| 50 | 200 | 131 | 116 | 88.55 |
| 51 | 202 | 125 | 67 | 53.60 |
| 52 | 209 | 106 | 64 | 60.38 |
| 53 | 222 | 119 | 105 | 88.24 |
| 54 | 219 | 125 | 109 | 87.20 |
| 55 | 201 | 124 | 79 | 63.71 |
| 56 | 216 | 132 | 107 | 81.06 |

Group no. 8: Atropine: 30 mg/10 ml/kg

| 57 | 212 | 119 | 58 | 48.74 |
| 58 | 219 | 126 | 50 | 39.68 |
| 59 | 208 | 120 | 45 | 37.50 |
| 60 | 201 | 131 | 61 | 46.56 |
| 61 | 209 | 118 | 52 | 44.07 |
| 62 | 214 | 129 | 58 | 44.96 |
| 63 | 210 | 126 | 53 | 42.06 |
| 64 | 206 | 125 | 52 | 41.60 |

What is claimed is:

1. A method for reducing increased volume and fluidity of stools and frequency of bowel movements relative to their usual pattern brought about by the administration of exogenous L-carnitine to an individual in need thereof, which comprises administering to said individual an effective amount of exogenous L-carnitine in the form of an equimolar amount of L-carnitine acid fumarate.

2. The method of claim 1, wherein a nutritionally dietetically or therapeutically effective amount of L-carnitine acid fumarate is administered.

3. The method of claim 1, wherein the L-carnitine acid fumarate is administered orally.

4. The method of claim 3, wherein the oral administration is in the form of a tablet, pill, capsule or power.

* * * * *